CHRYSANTHEMUM PLANT
Filed March 20, 1974
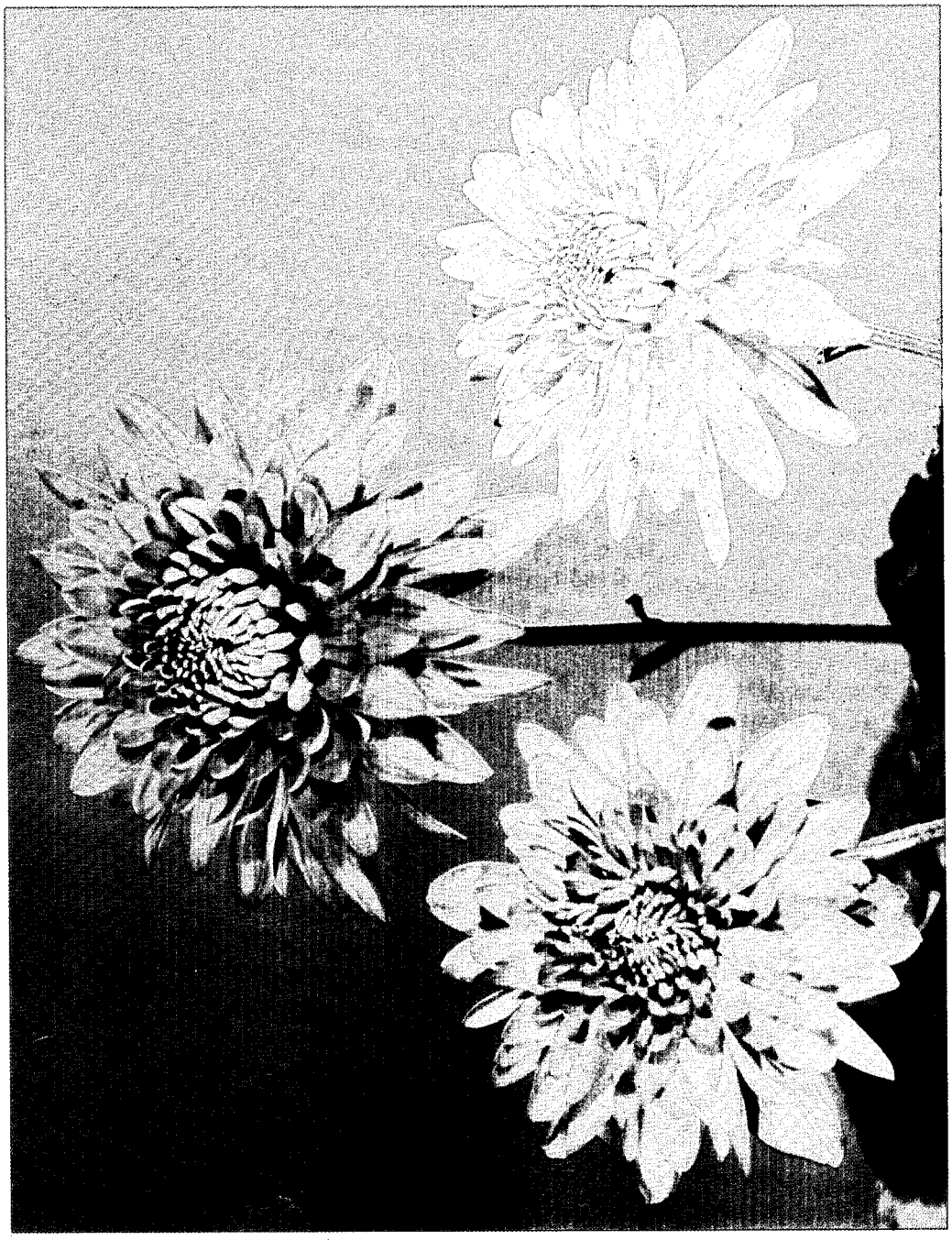

United States Patent

Plant Pat. 3,741
Patented July 8, 1975

3,741

CHRYSANTHEMUM PLANT

Charles B. Coward, Fort Myers, Fla., and Walter H. Jessel, Jr., Doylestown, and William E. Duffett, Akron, Ohio, assignors to Charles B. Coward, Fort Myers, Fla.

Filed Mar. 20, 1974, Ser. No. 453,034
Int. Cl. A01h *5/00*
U.S. Cl. Plt.—81 1 Claim

The present invention comprises a new and distinct cultivar of chrysanthemum plant known by the varietal name Beloved which is a sport of the cultivar known in the United States as Belair, which forms the subject matter of U.S. Plant Pat. No. 3,184, issued May 23, 1972.

The new cultivar is similar in many respects to Belair, having the same characteristics of:

1. Use as a cut spray.
2. Vigor and general growth habit.
3. Flowering response.
4. Flower size, form and form retention.

The new cultivar is distinguished from Belair by its more intense lavender color when grown under comparable conditions. The color of Belair is more lavender pink.

The new cultivar is also similar in many respects to Belrose, disclosed in our pending application Ser. No. 416,175, filed Nov. 15, 1973. Belrose is also a sport of Belair, with the flower color of Belrose being a noticeably darker purple than the lavender color of Beloved.

The new cultivar was discovered at Fort Myers, Florida, and when asexually reproduced by cuttings at Barberton, Ohio, has been found to retain its distinctive characteristics through successive propagations.

The new cultivar, when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern United States is from April through November 15; southeastern United States, March 15 through December 15; southwestern United States, March 15 through December 15; coastal California, March through December, and southern Florida under outdoor conditions November through April.

The accompanying photographic drawing shows the unique characteristics of the new cultivar, the color being as nearly true as possible with color illustrations of this type. The drawing is a comparison photograph, with the new cultivar Beloved appearing at the lower left, the cultivar Belair in the lower right, and the cultivar Belrose in the middle. Belrose is a noticeably darker purple as will be apparent from the drawing.

Color references in the following description are to the Munsell Book of Color, 1963 edition, and color comparisons are made with the cultivar Belair. Where only a single value or description for the color appears in the column under Beloved, the same value or description applies as well to Belair.

BOTANICAL CLASSIFICATION: *Chrysanthemum morifolium*

BLOOM:
- *size*—2¾"
- *fully expanded*—3¼"

- *borne*—terminal cluster of 8–12 on elongated pedicel according to culture
- *stems*—elongated pedicels 6"–10" in length branching from main stem
- *form*—decorative
- *permanence*—7–10 days

| | Beloved | Belair |
|---|---|---|
| *color:* | | |
| center of flower. | light yellow-green, 2.5GY8/6. | |
| base of petals | do | |
| inside of petals. | lavender, 2.5RP6/10 over light lavender, 2.5RP8/4. | lavender pink, 5RP8/4 over pale lavender, 5RP9/1. |
| reverse of petals. | greyed lavender, 2.5RP6/8 over pale lavender, 2.5RP9/2. | light lavender pink, 5RP9/2 over pale lavender, 5RP9/1. |
| tonality from a distance. | lavender | lavender pink. |
| discoloration | lavender, 2.5RP6/10 over light lavender, 2.5RP8/4. | lavender pink, 5RP8/4 over pale lavender, 5RP9/1. |

PETALS:
- *texture*—smooth
- *appearance and form*—slightly open at base, keeled at mid point, tapering to a blunt point
- *arrangement*—composite, whorled on a single receptacle
- *persistence*—resist shatter
- *fragrance*—typical chrysanthemum REPRODUCTIVE ORGANS:
- *stamen, anthers*—none to 20, more or less depending on culture
- *pollen*—none to scant
- *arrangement*—clustered in center of flower, if present
- *styles*—present in both ray and disc floret
- *length*—short
- *ovaries*—at the base of petal attached to receptacle PLANT:
- *form*—herbaceous
- *growth*—upright
- *height*—approximately 36"–42" given 1–2 long day weeks with a response of 9 weeks, and 10–11 week total crop time, as defined in the timetables of Yoder Brothers, Inc., Barberton, Ohio, for the various seasons of the year
- *spread*—none when grown single stem to slight when pinched FOLIAGE:
- *top side*—green, 7.5GY3/4
- *size*—7"–9" long, 4"–5" wide
- *quantity*—numerous
- *shape*—spatulate lobed
- *texture*—coarse
- *ribs and veins*—prominent
- *edge*—deeply indented
- *serration*—slight
- *under side*—greyed green, 5GY4/4
- *stipules*—prominent at base of petiole

We claim:

1. A new and distinct cultivar of chrysanthemum characterized particularly as to its uniqueness when compared to the parent cultivar Belair by its more intense lavender coloration.

No reference cited.

ROBERT E. BAGWILL, Primary Examiner